United States Patent
Martin et al.

(10) Patent No.: US 6,645,126 B1
(45) Date of Patent: Nov. 11, 2003

(54) PATIENT REHABILITATION AID THAT VARIES TREADMILL BELT SPEED TO MATCH A USER'S OWN STEP CYCLE BASED ON LEG LENGTH OR STEP LENGTH

(75) Inventors: Matthew Martin, Remsenberg, NY (US); Edward Behan, Blue Point, NY (US); Joseph Chilleme, Kings Park, NY (US)

(73) Assignee: Biodex Medical Systems, Inc., Shirley, NY (US)

( * ) Notice: Subject to any disclaimer, the term of this patent is extended or adjusted under 35 U.S.C. 154(b) by 0 days.

(21) Appl. No.: 09/546,593

(22) Filed: Apr. 10, 2000

(51) Int. Cl.[7] .............................................. A63B 22/00
(52) U.S. Cl. .............................. 482/54; 482/51; 482/3
(58) Field of Search ................................ 482/51, 54, 3

(56) References Cited

U.S. PATENT DOCUMENTS

| | | |
|---|---|---|
| 4,708,337 A | 11/1987 | Shyu |
| 4,890,495 A | 1/1990 | Slane |
| 4,943,050 A | 7/1990 | Smith |
| 5,052,406 A | 10/1991 | Nashner |
| 5,269,318 A | 12/1993 | Nashner |
| 5,299,454 A | 4/1994 | Fuglewicz |
| 5,314,391 A * | 5/1994 | Potash et al. .................. 482/54 |
| 5,474,087 A | 12/1995 | Nashner |
| 5,476,103 A | 12/1995 | Nashner |
| 5,551,445 A | 9/1996 | Nashner |
| 5,623,944 A | 4/1997 | Nashner et al. |
| 5,697,791 A | 12/1997 | Nashner |
| 5,833,584 A | 11/1998 | Piaget et al. |
| 5,848,594 A | 12/1998 | Matheson |
| 5,955,667 A | 9/1999 | Fyfe |
| 6,050,822 A * | 4/2000 | Faugn .......................... 482/54 |

FOREIGN PATENT DOCUMENTS

EP 0176277 A 4/1986

OTHER PUBLICATIONS

Biomechanics of Overground versus Treadmill Running, Medicine and Science in Sports 4:233–240, Nelson, et al. (1972).

The Process of Habitation to Treadmill Walking: A kinetic Analysis, Perceptual and Motor Skills 4:659–666; Charteris, et al. (1978).

A Speed–Related Kinematic Analysis of Overground and Treadmill Walking in: Traves, et al. (1983).

Biomechanics XI, Human Kinetics Publishers, Champaign, pp. 423–426;in Winter, et al. (eds.).

Biomechanics of Overground Versus Treadmill Running, Medicine and Science in Sports 4:233–240; Nelson, et al. (1972).

The Process of Habitation to Treadmill Walking: a Kinetic Analysis, Perceptual and Motor Skills 47:659–666) Charteris, et al. (1978).

Copy of Partial European Search Report—EP 01 30 3360.0-1526 dated Jan. 10, 2003.

* cited by examiner

Primary Examiner—Glenn E. Richman
(74) Attorney, Agent, or Firm—Gibbons, Del Deo, Dolan, Griffinger & Vecchione

(57) ABSTRACT

The invention is directed to a gait rehabilitation aid and to a method for aiding gait rehabilitation. The gait rehabilitation aid resides in a treadmill having a belt which speed matches a user's own step cycle based on let length and which provides feedback in the form of an evaluation with respect to the user's length, cadence, gait velocity and gait pattern. A controller that is responsive to a user input device is employed to input information that inputs information pertaining to any one of cadence and leg length sets the belt speed to match an appropriate step cycle. In addition, footprints are scrolled on a display together with foot falls that correspond to actual heel strike events on the treadmill belt. The footprints appear in accordance with the user's own step cycle.

25 Claims, 17 Drawing Sheets

STEP LENGTH

BIODEX

RTM500
GAIT TRAINER

BIODEX SW 945 - 385 - E617
VOM VERSION 1.00
PRINTER: HP612
LB VERSION 1.06

PRESS START TO CONTINUE

FIGURE 4

GAIT TRAINING SETUP

| | | |
|---|---|---|
| AGE | 40 | YRS. |
| SEX | M | M/F/CHILD |
| HISTOGRAM SAMPLE QTY | 3 | SAMP |
| DISPLAY TYPE | H | FT/H |
| RIGHT LEG LENGTH | 72 | CM |
| LEFT LEG LENGTH | 72 | CM |
| TARGET STD. DEV. | 10 | CM |
| TONE ON OFF | OFF | |
| BIOFEEBACK CYCLE ON | 30 | SEC |
| OFF | 15 | SEC |
| TEST DURATION | 5:00 | MIN / SEC |

SELECT △

SELECT ▽

0.00 IS CONTINUOUS

[NEXT SCREEN] TO CONTINUE

FIGURE 6

SCREEN NUMBER: --

TEST RESULTS

TOTAL EXERCISE TIME: [2:00] MINUTES
TOTAL DISTANCE: [132] METERS
AVERAGE HEART RATE/SP02: [95] BPM [97] SP02
AVERAGE SPEED: [1.10] METERS/SEC
AVERAGE STEP CYCLE: [0.82] CYCLES/SEC

|  | RIGHT | LEFT |
|---|---|---|
| ENTERED LEG LENGTH: | [0.840] M | [0.840] M |
| AVERAGE STEP LENGTH: | [0.65] M | [0.70] M |
| COEFFICIENT OF VARIANCE: | [25] % | [29] % |
| RT/LT TIME DISTRIBUTION: | [52] % | [48] % |
| AMBULATION INDEX: | [96] | GOAL 100 |

| PRESS | START | TO PRINT NUMERICAL REPORT |
|---|---|---|
| PRESS | ENTER | TO PRINT GRAPHICAL REPORT |
| PRESS | PREV | TO RETURN TO TEST SCREEN |
| PRESS | NEXT | TO RETURN TO MAIN MENU |

SCREEN NUMBER 45

FIGURE 9

NORMATIVE GAIT PARAMETER TABLES MALE

| AGE<br>YRS | CADENCE<br>STEPS/MIN | CYC TIME<br>SECONDS | STEP LEN<br>METERS | SPEED<br>M/SEC |
|---|---|---|---|---|
| 13 - 14 | 100 - 149 | 0.81 - 1.20 | 1.06 - 1.64 | 0.95 - 1.67 |
| 15 - 17 | 96 - 142 | 0.85 - 1.25 | 1.15 - 1.75 | 1.03 - 1.75 |
| 18 - 49 | 91 - 135 | 0.89 - 1.32 | 1.25 - 1.85 | 1.10 - 1.82 |
| 50 - 64 | 82 - 126 | 0.95 - 1.46 | 1.22 - 1.82 | 0.96 - 1.68 |
| 65 - 80 | 81 - 125 | 0.96 - 1.48 | 1.11 - 1.71 | 0.81 - 1.61 |

PREVIOUS SCREEN: TO RETURN
NEXT: FOR NEXT SCREEN
START: TO PRINT RESULTS

FIGURE 10

FIGURE 12 PAGE 1 OF 1
BIODEX GAIT TRAINING EXERCISE GRAPHIC REPORT
NAME: _____  DATE: _____
HEIGHT: _____  AGE: ___40___
WEIGHT: _____  SEX: ___MALE___
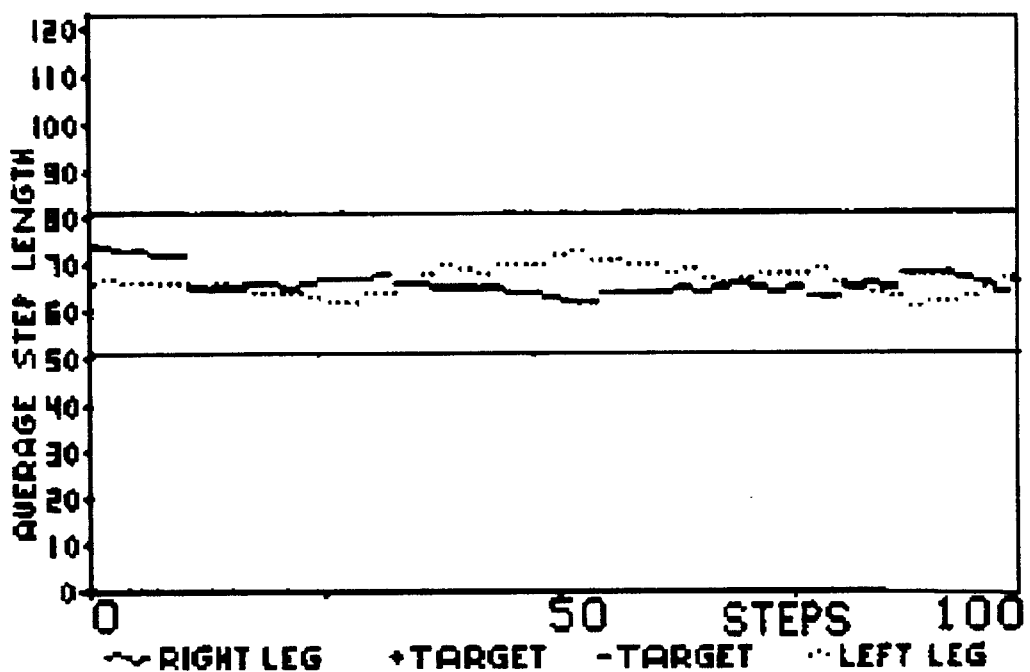
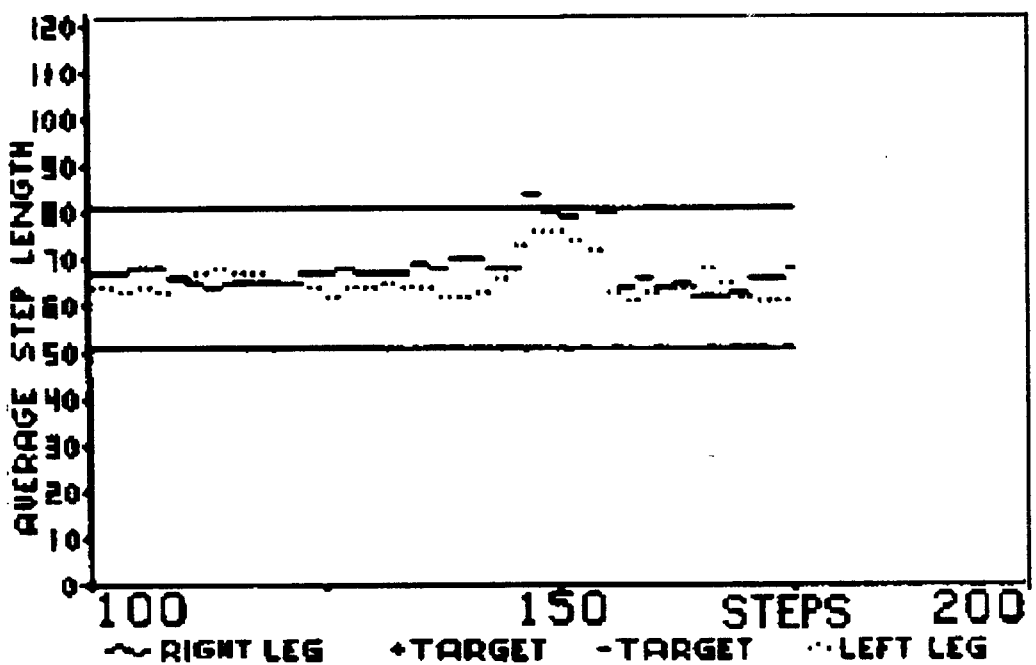

PATIENT REHABILITATION AID THAT VARIES TREADMILL BELT SPEED TO MATCH A USER'S OWN STEP CYCLE BASED ON LEG LENGTH OR STEP LENGTH

BACKGROUND OF THE INVENTION

1. Field of the Invention

The invention relates to a rehabilitation aid in the form of a treadmill whose belt speed is set to a patient's own step cycle based on leg length or step length. The treadmill helps rehabilitation of stroke, spinal cord, head injury, amputees, orthopedic, neurologic and vestibular patients by improving their gait characteristics, step frequency and stride length to match the user's own step cycle as a function of leg length or step length.

2. Discussion of Related Art

U.S. Pat. No. 5,623,944, entitled METHOD FOR CHARACTERIZING GAIT, issued Apr. 29, 1997 Nashner. This patent contains a description of the Categories of Gait and the characterization of Gait Using A Treadmill. The description is informative in describing the direction that the state of the art has taken and so is reproduced here.

Categories of Gait

The phases of human gait have been described by many authors; some examples include, Inman, et al. (1981) "Human Walking," Williams and Wilkins, Baltimore; Winter, D. A. (1983) "Biomechanical Motor Patterns in Normal Walking," Journal of Motor Behavior 15:302–330; and Winestein, et al. (1989) "Quantitative Dynamics of Disordered Human Locomotion: a Preliminary Investigation," (Journal of Motor Behavior 21:373–391). Human gait may be classified in general categories of walking and running. During walking, at least one foot is always in contact with the support surface and there are measurable periods of time greater than zero during which both feet are in contact with the support surface. During running, there are measurable periods greater than zero during which time neither foot is in contact with the support surface and there are no times during which both feet are in contact with the support surface.

Walking can be separated into four phases, double support with left leg leading, left leg single support, double support with right leg leading, and right leg single support. Transitions between the four phases are marked by what are generally termed "heel-strike" and "toe-off" events. The point of first contact of a foot is termed a "heel-strike", because in normal adult individuals the heel of the foot (the rearmost portion of the sole when shoes are worn) is usually the first to contact the surface. However, heel-strike may be achieved with other portions of the foot contacting the surface first. During running normal adult individuals sometimes contact a surface with the ball of the foot (forward portions of the sole when shoes are worn). Individuals with orthopedic and/or neuromuscular disorders may always contact the surface with other portions of the foot or other points along the perimeter of the sole when shoes are worn. Similarly, while the ball and toes of the foot are the last to contact the surface at a toe-off event in normal adults, a patient's last point of contact may be another portion of the foot. Thus, regardless of the actual points of contact, the terms heel-strike and toe-off refer to those points in time at which the foot first contacts the support surface and ceases to contact the surface, respectively.

Characterization of Gait Using a Treadmill

Treadmills allowing a subject to locomote over a range of walking and running speeds within a confined space have been described in the prior art (Traves, et al. (1983) "A Speed-Related Kinematic Analysis of Overground and Treadmill Walking"; Winter, et al. (eds.) Biomechanics XI, Human Kinetics Publishers, Champaign, pp. 423–426; Nelson, et al. (1972) "Biomechanics of Overground Versus Treadmill Running," Medicine and Science in Sports 4:233–240; and Charteris, et al. (1978) "The Process of Habitation to Treadmill Walking: a Kinetic Analysis," Perceptual and Motor Skills 47:659–666). A treadmill allows the difficulty of gait to be precisely set by independently controlling the belt speed and the inclination of the belt. The subject can be maintained in a fixed position relative to the measuring surface underlying the treadmill belt by coordinating the speed of gait with the speed of the treadmill belt movement. Several prior art research studies have described treadmills in which a single forceplate with mechanically coupled force transducers has been mounted directly beneath the treadmill belt. Kram et al., in their paper "A Treadmill-Mounted Force Platform", Journal of The American Physiological Society, 1989, pages 1692–1698, describe a treadmill having a single forceplate. This paper is enclosed herewith and hereby incorporated herein by reference. The single forceplate provided continuous measurement of the forces exerted by the combined actions of the two feet on the overlying treadmill belt during gait.

It is sometimes desirable to determine the position of the center of force in relation to coordinates of specified anatomical features of the foot when the foot is in contact with a surface which is moving in relation to a fixed force sensing surface. This occurs, for example, when the foot is contacting the moving belt of a treadmill which overlays a force sensing surface. To determine the position of the center of force in relation to coordinates of the specified anatomical features of the foot, two coordinate transformations are performed. One, the position of the center of force is determined in relation to coordinates of the moving treadmill belt. Two, the position of the moving treadmill belt is determined in relation to coordinates of the specified anatomical feature of the foot. To perform the first of these coordinate transformations requires knowledge of the treadmill belt position in relation to the fixed force sensing surface position on a continuous basis. To perform the second of these two coordinate transformations requires knowledge of the position of the specified anatomical features of the foot in relation to the treadmill belt. Since the position of the foot and its anatomical features does not change in relation to the treadmill belt following each heel-strike event and before the subsequent toe-off of that foot, the position of the specified anatomical features of the foot needs to be determined only once at heel-strike for each step.

One method to determine the position of the treadmill belt on a continuous basis in relation to the fixed force sensing surface is to use one of several sophisticated commercial treadmill systems described in the prior art which measure the anteroposterior speed of the moving treadmill belt on a continuous basis, and which provide the means to regulate the belt anteroposterior speed on a continuous basis. One example of a commercially available treadmill system with automatic speed control and belt speed measurement systems is the Star Trac 2000, manufactured by Unisen, Inc., Tustin, Calif. When one of these treadmill systems is used, the information necessary to determine the continuous position of the treadmill belt in relation to the underlying forceplate is obtained by performing mathematical integration of the belt speed signal on a continuous basis.

There are methods described in the prior art which can be used to determine, at the time of heel-strike, the position of the moving treadmill belt in relation to the specified anatomical features of the foot. One method is to use one of several commercially available optical motion analysis systems. Two examples of commercially available motion analysis systems which describe applications for tracking the motions of identified points on the human body during locomotion include the ExpertVision system manufactured by Motion Analysis Corp., Santa Rosa, Calif. and the Vicon system manufactured by Oxford Medilog Systems, Limited, Oxfordshire, England. In accordance with this method, one or more optical markers are placed on the specified anatomical features of the foot. One or more additional markers are placed on the treadmill belt at predetermined positions. The number and placement of the optical markers on the anatomical feature and the treadmill belt determine the accuracy of the measurement as specified by the systems manufacturers. At the time of heel-strike, the positions of the treadmill belt marker or markers are then determined in relation to the positions of the anatomical feature marker or markers in accordance with methods specified by the system manufacturer.

U.S. Pat. No. 5,623,944 describes devices and methods for separately determining quantities related to the force exerted by each foot against the treadmill belt support surface at all phases of the step cycle and a means for determining quantities related to the position of the center of force exerted by each foot in relation to a fixed point on the treadmill belt or in relation to a specified anatomical feature of the foot or to train normals to alter their gait patterns. A method and apparatus for characterizing the gait of a subject is revealed that uses a treadmill having a movable support surface with multiple transducers mounted beneath the movable support surface. The subject performs locomotion on the movable surface. The computer accepts a series of signals from each transducer and identifies the occurrence of heel-strike and toe-off. The computer identifies the subject's activity as walking or as running. The computer identifies two non-contiguous groups of transducers that are measuring a force greater than zero associated with the two feet and calculates quantities related to the forces exerted by each foot during each phase of walking or running.

The present inventors, however, have made some observations as follows under Gait Training.

One of the most evident indicators of overall health is gait speed. People with gait problems have unsymmetrical or shortened step lengths, and are typically stroke, spinal cord, head injury, amputees, orthopedic, neurologic or vestibular patients. Such patients may strive to attain normal walking patterns, but require improvement in their balance and coordination, strength and range of motion, and cardiovascular capacity and endurance.

There are two methods in which a patient can increase gait speed. One is to increase stride length and the other is to increase step frequency. Regardless of step length, people are most comfortable walking at a cadence of about 2 steps per second. The ideal step length may be determined by measuring the patient's leg length.

Patients may have a wide stance shuffle. Such patients may assume that this gait pattern is not the result of weakness, but instead from a lack of confidence and a fear of falling. There is a need, therefore, to provide an environment that is safe and controlled that helps such patients regain that confidence.

Conventional treadmills must be set to a constant speed. There is no way to determine the user's cadence at these speeds. Indeed, a comfortable walking speed will differ depending on the step length. To be considered a community ambulator, patients must walk at least 0.6 meters/second. This value is a guideline for functional independence. There is a need for an apparatus to evaluate a patient's stride length, cadence, gait velocity and gait pattern and then provide quantified documentation so as to help such patients become a community ambulator.

Therapists who work with patients who require rehabilitation of their gait need to document important gait parameters of such patients so as to assess improvement over time. Clear, concise quantified documentation reinforces the benefits of therapy to the patient, healthcare providers and third party payers. Further, both the therapists and the patients need the rehabilitation process to take place in an environment that is safe to both.

It would be desirable to provide an apparatus and technique that fulfills all these needs by evoking the right stride length and step cycle for the patient using the apparatus.

BRIEF SUMMARY OF THE INVENTION

One aspect of the invention resides in a treadmill whose belt speed matches a user's own step cycle based on leg length or step length and which provides evaluation with respect to the user's stride length, cadence, gait velocity and gait pattern. A pattern of ideal foot prints, which are shown in accordance with the user's own step cycle, are scrolled on a display screen together with representation of foot falls that correspond to actual heel strike events on the treadmill.

BRIEF DESCRIPTION OF THE SEVERAL VIEWS OF THE DRAWING

For a better understanding of the present invention, reference is made to the following description and accompanying drawings, while the scope of the invention is set forth in the appended claims.

FIG. 4 is a screen display that appears when the embodiment of the invention is first turned on.

FIG. 6 is a screen display showing a gait training setup.

FIG. 9 is a screen display of exercise data.

FIG. 10 is a screen display of normative data for key gait parameters.

FIG. 12 is a screen display of an exercise graphic report.

DETAILED DESCRIPTION OF THE INVENTION

Figure 1:
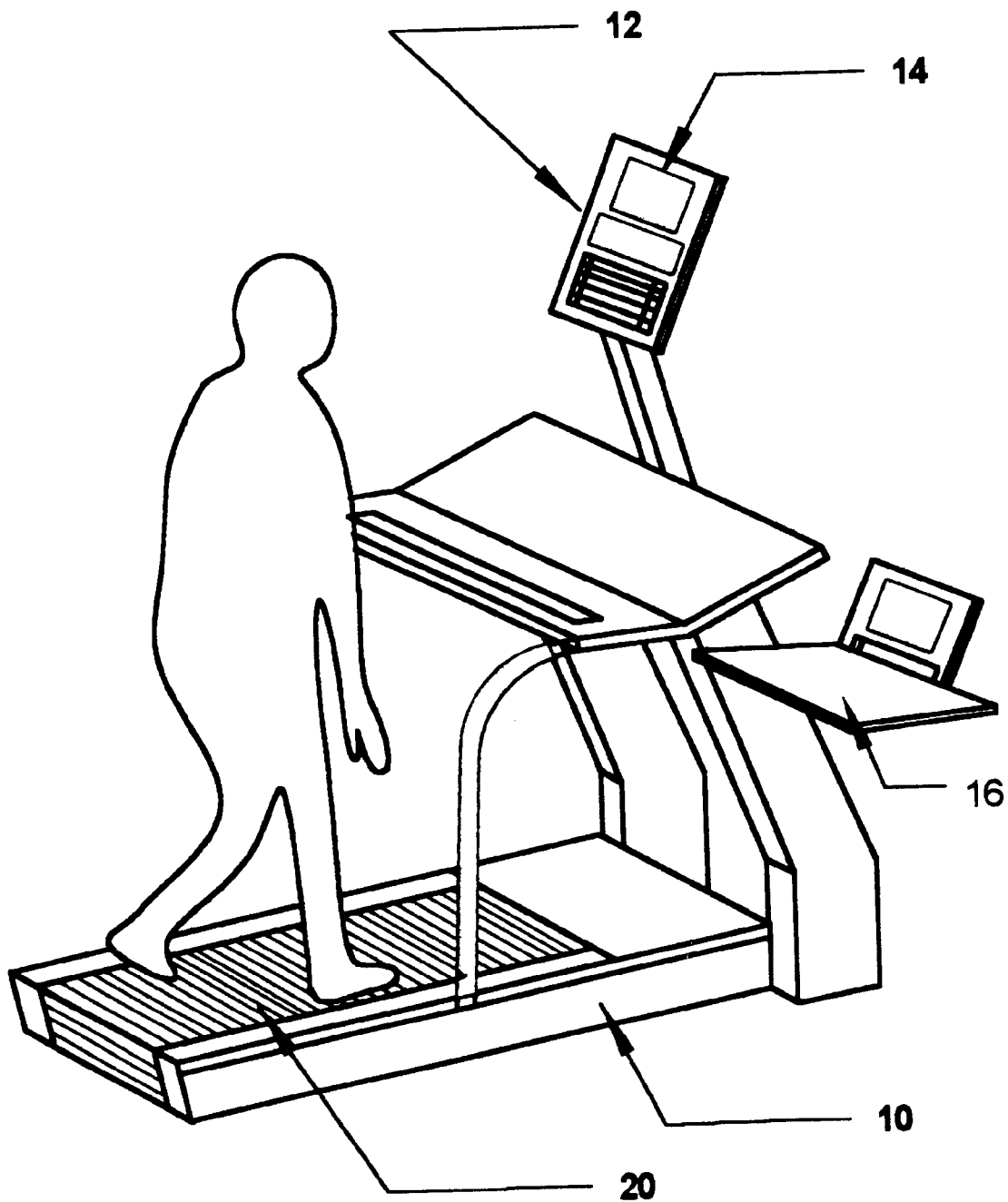
FIG. 1 is a perspective view of the treadmill whose belt speed matches the step cycle of a patient based on leg length in accordance with an embodiment of the invention.
Figure 2:
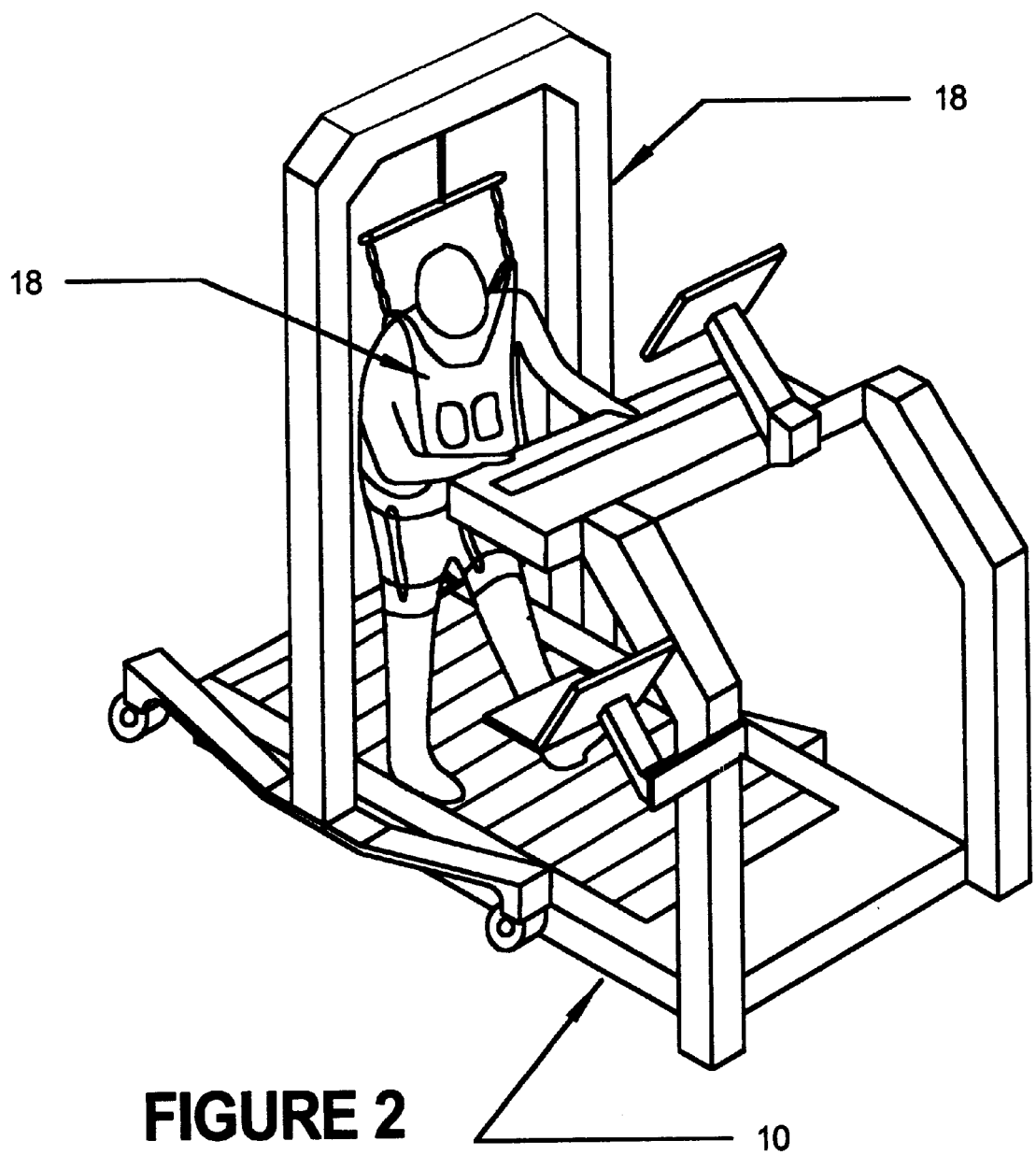
FIG. 2 is a perspective view of the treadmill of FIG. 1 used with an unweighing system for partial weight bearing therapy in accordance with a further embodiment of the invention.

Turning to the drawings, FIG. 1 shows a treadmill 10 having a control panel 12, a screen display 14 and a printer 16. FIG. 2 is the same as that of FIG. 1, but also shows an unweighing system 18 for partial weight bearing therapy. Both embodiments are commercially available from Biodex Medical of Shirley, N.Y. by requesting BIODEX GAIT TRAINER TREADMILL with or with the BIODEX UNWEIGHING SYSTEM.

Figure 3:
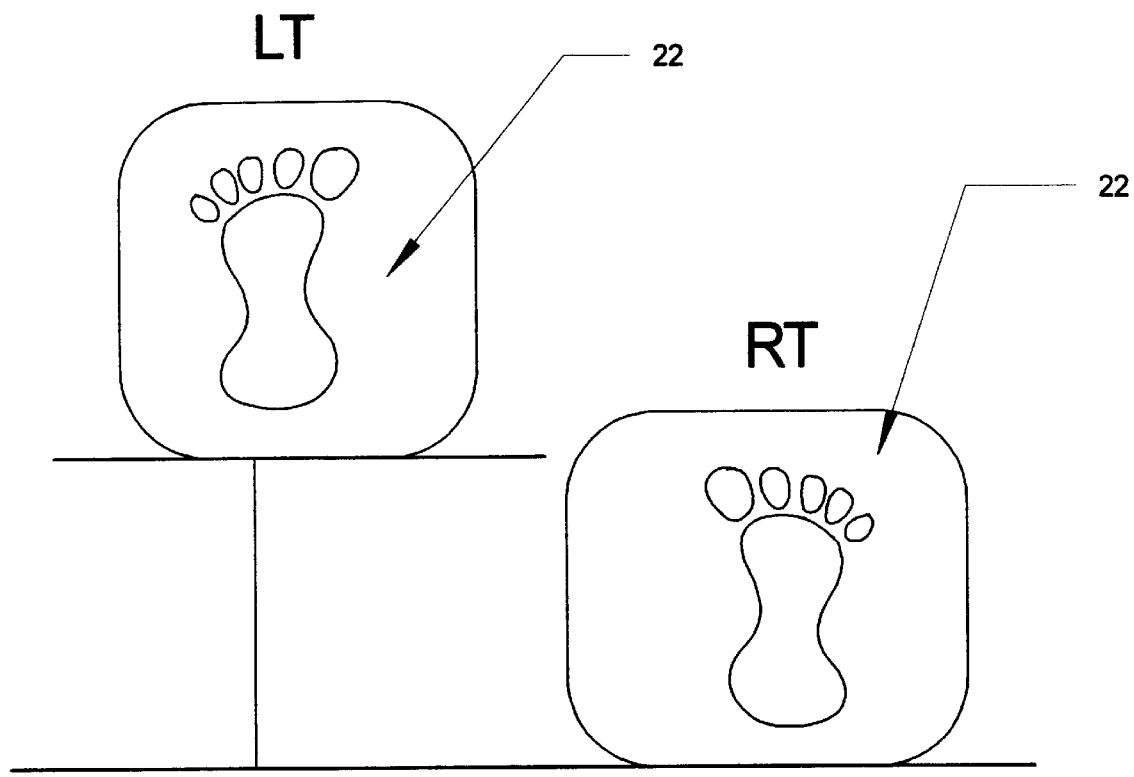
FIG. 3 is a schematic representation of step length.

The treadmill 10 features an instrumented walking surface 20. Representations of actual footfalls 22 (FIG. 3) during walking are displayed on the screen display 14. The step length is the distance between successive foot falls. The control panel 12 provides the ability to control belt speed to match a patient's step cycle.

By sensing left or right footfalls in the instrumented walkway 20, the present invention allows for the determination of the step length (by knowing the speed) and cadence. Using this information, the treadmill speed can be automatically controlled or changed in response to this information to produce a comfortable cadence. The ideal step length can be exactly preset by entering leg length measurements into the treadmill display. The desired step cycle (cadence) is preset by entering it into the control panel.

Further, audio and visual feedback may be turned on or off to help reinforce training retention. Visual prompts for corrective action and positive reinforcement may be displayed. Footfall targets are normalized to limb length for accurate step cycle sequencing and depicted as ideal foot prints that scroll down the screen display 14. The printer 16 may be actuated to print an exercise summary report upon completion to track progress and document outcome. This report is exemplified as follows:

| BIODEX GAIT TRAINING EXERCISE SUMMARY | | | |
|---|---|---|---|
| NAME _____ | | Date _____ | |
| HEIGHT _____ | | AGE __40__ | |
| WEIGHT _____ | | SEX __MALE__ | |
| | | ACTUAL | NORMAL RANGE |
| TOTAL EXERCISE TIME | 2:00 Minutes | | |
| Total Distance | 132 Meters | | |
| Average Heart Rate/SpO$_2$ | 95 BPM | 97 SpO$_2$ | |
| Avg Walking Speed | 1.10 Meters/Second | | |
| Average Step Cycle | 0.82 Cycles/Second | | |
| | Right | Left | |
| Entered Leg Length | .840 m | .840 m | |
| Average Step Length | .65 m | .70 m | |
| Coefficient of Variance | 25% % | 29 % | |
| Rt/Lt time distribution | 52% % | 48 % | |
| AMBULATION INDEX | 96 | | Goal = 100 |

Ambulation index is a composite score relative to 100 based on foot to foot time distribution ratio and average step cycle.
Comments:
_____
_____

Biofeedback is provided in accordance with the invention to help the patient improve gait speed and gait characteristics of increased step frequency and stride length to help the patient attain an optimal level of locomotor ability and independence. The biofeedback helps patients alter their step length to make it symmetrical and normal for their leg length. An integrated report system for quantified outcome measurement is provided to assist the patient, therapist and third party payers alike.

Unlike conventional treadmills, the present invention equates belt speed to a functional gait parameter, namely, the patient's own step cycle and step length based on leg length. By matching the belt speed to the patient's own step cycle and ideal step length, the present invention triggers enough of a neurological response to evoke a normal gait pattern with good stride length. Through repetition, patients are unconsciously relearning to walk in sequence by helping patients increase both frequency and stride length in a symmetrical fashion.

The present invention evaluates a patient's stride length, cadence, gait velocity and gait pattern to provide quantified documentation, which is useful as a measure for ambulation. To be considered a community ambulator, patients must walk at least 0.6 meters per second.

Whether the patient is neurologically impaired or an orthopedic patient, the present invention evokes the right stride length for that patient. The present invention is useful for rehabilitation of the normal stride length for stroke, spinal cord, head injury, amputees, orthopedic, neurologic and vestibular patients. It helps such patients develop balance and coordination, strength and range of motion, normal walking patterns, and increased cardiovascular capacity and endurance, as well as providing a safe environment for patients and therapists and documentation of important gait parameters.

The treadmill of the present invention preferably uses a 2 horsepower motor with 4Q-pulse modulation control to provide a forward speed range of 0–8 mph (0–12.9 km/h) and a reverse speed range of 0–3 mph (0–4.8 km/h) in increments of 0.1 mph (0.16 km/h). The walking surface deck is preferably of an impregnated high density composite fiber. Since it always starts at 0 mph with increments of 0.1 mph, no belt straddle need arise. Preferably, the treadmill is available from Biodex Medical Systems under model number RTM 500.

Operation of the control of the present invention is menu driven, with the use of a "Next Screen/Previous Screen" type flow via dedicated keypad buttons. Preferably, an NEC V25 processor is used with a Yamaha V6366C LCD driver. Inputs include key presses, the gait L/R indicator, a pulse rate/ oxygen monitor input and basic speed reporting from the treadmill controller board. Other dedicated keys include "Start", "Stop" & "Enter". Four softkeys enable selection/ parameter modifications.

Figure 5:
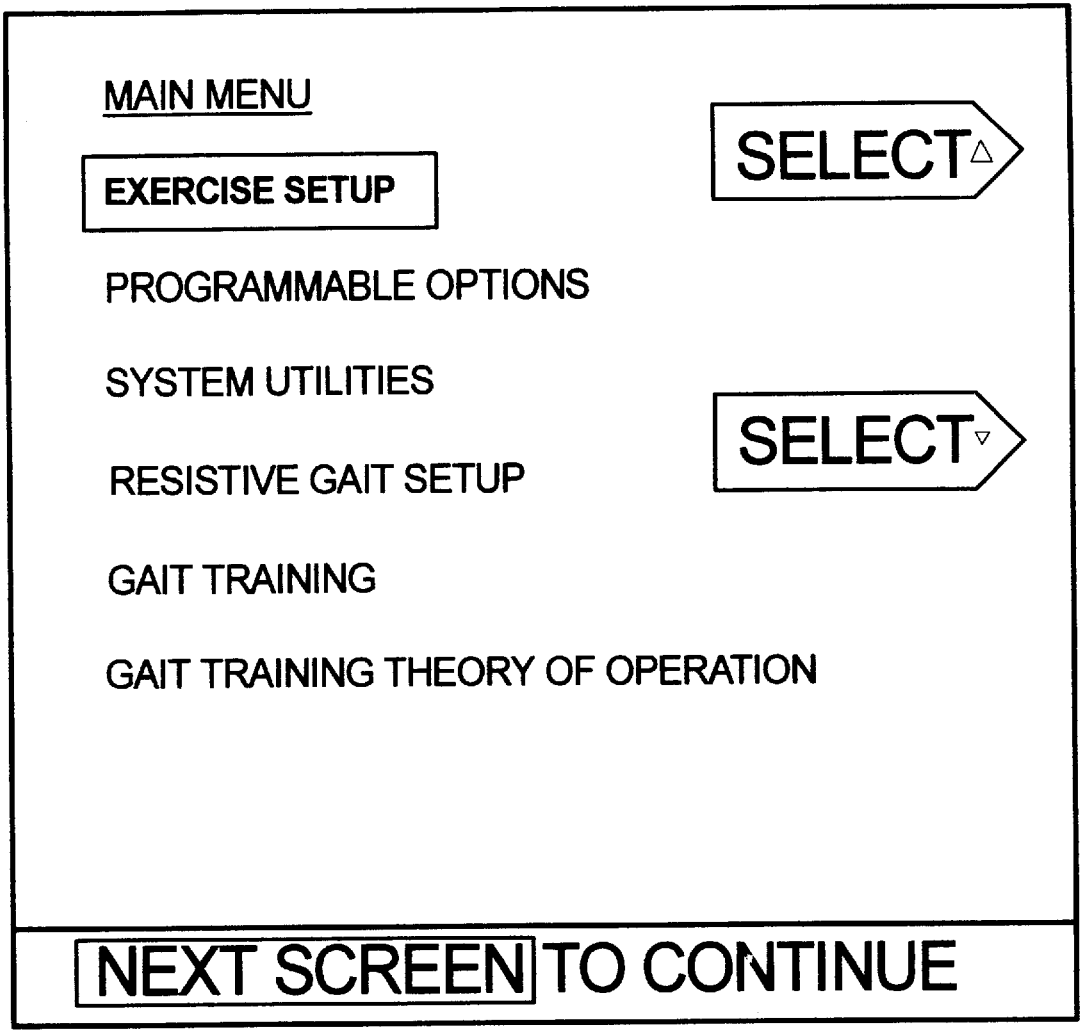
FIG. 5 is a screen display showing a main menu.

In use, the present invention is accessible by selecting the start option that appears on the screen when the treadmill is first powered up (FIG. 4). Selecting start on the first screen (FIG. 4) calls the main menu screen (FIG. 5). The option for gait training is selected from the menu driven control, (FIG. 5) by pressing the appropriate select arrow keys until the gait training option is highlighted (FIG. 5). By pressing NEXT SCREEN TO CONTINUE while the Gait Trainer option is selected, the display switches to the Gait Training set-up screen of FIG. 6.

The ideal step length is determined by measuring the patient's leg length and entering leg length information into the treadmill display screen. The treadmill is then started and speed is automatically controlled to produce the proper cadence. The display may show an indication of proper step lengths as "foot prints" scrolling down the screen or other means. The patient tries to obtain the proper step lengths to match the display by making his/her foot falls (displayed on the screen) match the ideal footprints scrolling down the screen. The speed of the treadmill may be adjusted to a lesser cadence to maintain a comfortable cadence if the patient cannot keep up with the ideal speed that is based on the leg length and ideal cadence.

To enter leg lengths for the right and left legs, measurements are entered such as in centimeters. The step length to leg length ratio is between 0.69–0.86. The normal step length is marked on the performance screen (FIG. 7) as a line at the heel of the right foot and a line at the heel of the left foot. Although a diagonal measurement from the center of right heel to the center of the left heel is the most reliable type of measurement, such is difficult to implement so the distance the belt traverses between successive heel strikes will be treated as the step length.

For visual feedback, the allowable step length deviation from target may be set and for audio feedback, the volume control for the metronome tone generator interval may be set and either actuated or turned off. Patients may become dependent on the biofeedback, so a biofeedback intermittent on/off cycle time may be actuated to turn the biofeedback on and off intermittently.

Figure 7:
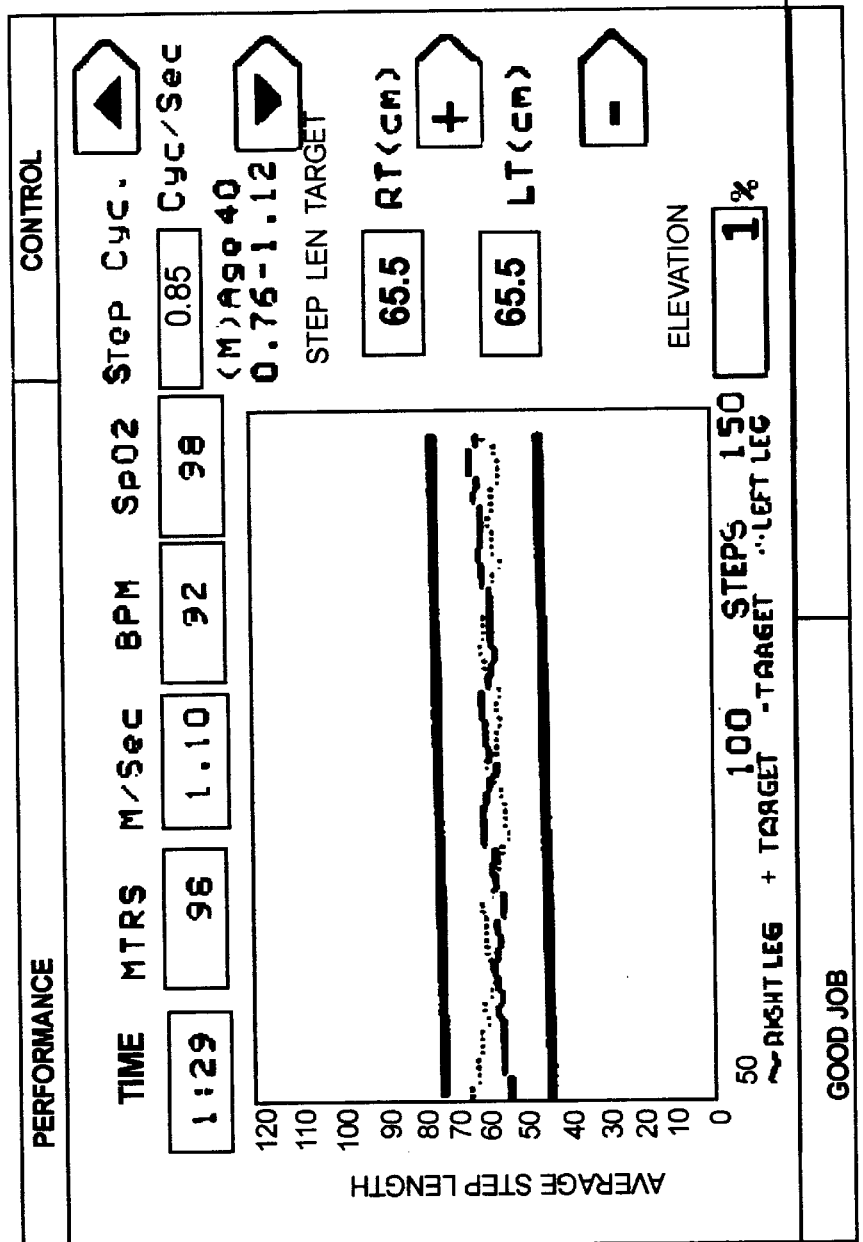
FIG. 7 is a screen display showing gait training performance and control.
Figure 8:
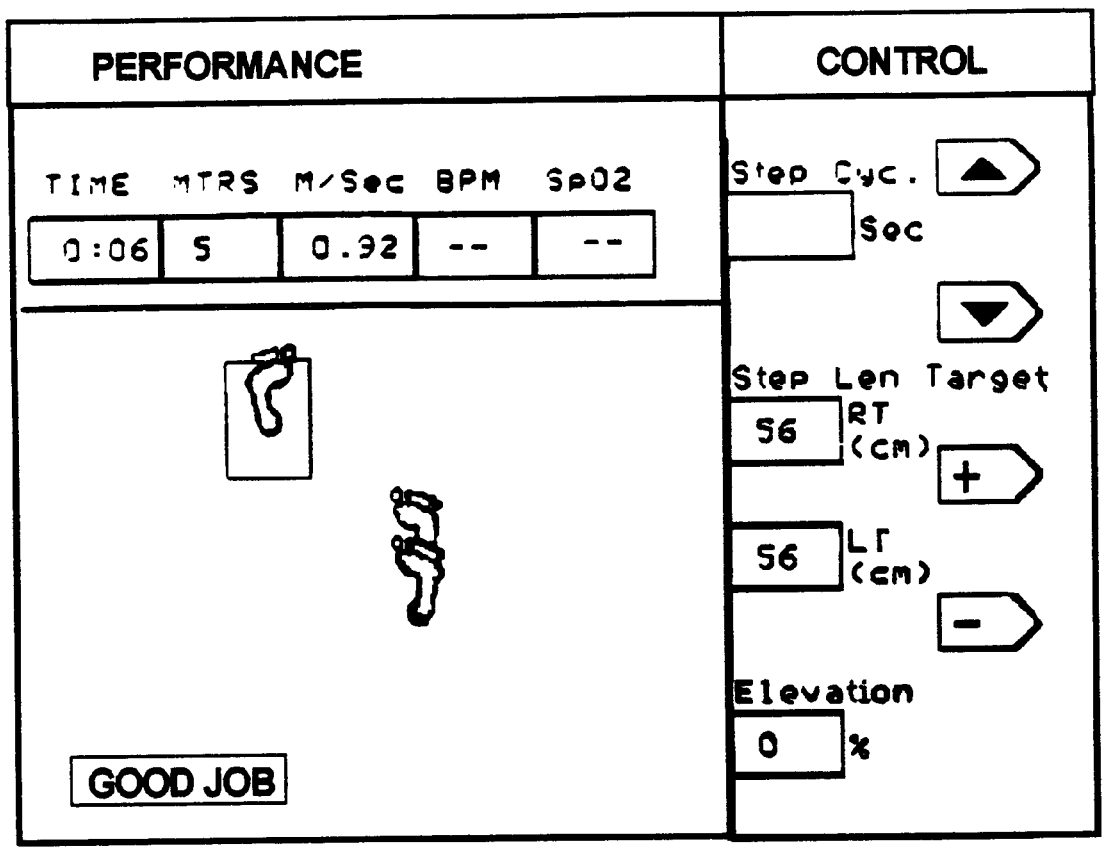
FIG. 8 is a screen display showing a pause screen.

The gait training performance may be visualized on the screen (FIG. 7). The four softkeys on the right are used for selecting and changing parameters, namely the up and down arrow heads, the plus sign and the minus sign. One entire stride length should be displayed. The variance of the actual footfall from the target should be monitored and the coefficient of variance calculated. A visual prompt message may be given that advises the patient using the present invention to either make an adjustment if the actual footfall is outside the target by more than a predetermined allowable range of no less than 3 cm or make a reward for good performance if the patient's actual footfall is within the target by the predetermined range (FIG. 8).

For instance, if the left foot is outside the target by the predetermined range, a message should appear advising that the right foot go faster. If the right foot is outside the target, then the message should advise the left foot go faster. A reward message may be simply GOOD JOB! (FIG. 8)

Another screen display status results may be shown. (FIG. 9). These results include, but are not limited to: total exercise time, total distance, and average speed. Other results that may be shown appear in FIG. 9. The printed results may appear in the print out as completion of the following table (blanks are printed in based on the results).

Exercise Data Screen: SUMMARY OF PREVIOUS TEST (PRINTABLE)

| | | | |
|---|---|---|---|
| Total exercise Time | | ____ min | |
| Total distance | | ____ meters | |
| Average SpO$_2$ | | ____ % SpO$_2$ | |
| Average Heart Rate | | ____ bpm | |
| Average Step Cycle | | ____ seconds | |
| | Right | | Left |
| Entered Leg Length | ____ cm | | ____ cm |
| Normal Step Length | ____ cm | | ____ cm |
| Coefficient of Variance | ____ | | ____ |
| Rt/Lt time distribution | ____ % | | ____ % |
| AMBULATION INDEX | | ____Goal 100 | |

Press START to Print NEXT SCREEN to return to Main Menu.

Definitions:

Total time: The total duration of the exercise session

Total distance: The total distance covered in meters. This population is not a mileage group.

Average Heart Rate: Average HR for the exercise time. If equipped.

Average SpO$_2$: Level of dissolved oxygen in the blood stream.

Average Step Cycle: The average time in seconds from one footfall heel strike to another then back to the first (time for 2 steps =step cycle).

Entered leg length RT and LT from screen 3.

Average Step length, RT and LT: From the actual patient footfall.

Normal Step length, RT and LT: from the comparative table.

RT/LT Time distribution: The percent time from the whole time spent on right foot versus left foot.

AMBULATION INDEX: Is defined as a single number that represents a comparison to a normal performance goal. It has to base itself from 100, where 100 is the goal. The AI should include the following:

RT/LT Time distribution: Ideal ratio is 1:1

RT CV LT CV: Ideal ratio is 1:1

Step Cycle: Ideal goal is 1 cycle per second.

FIG. 10 shows a screen display of normative data for key gait parameters. Such screen displays are available for a male, female or for a child.

Figure 11:
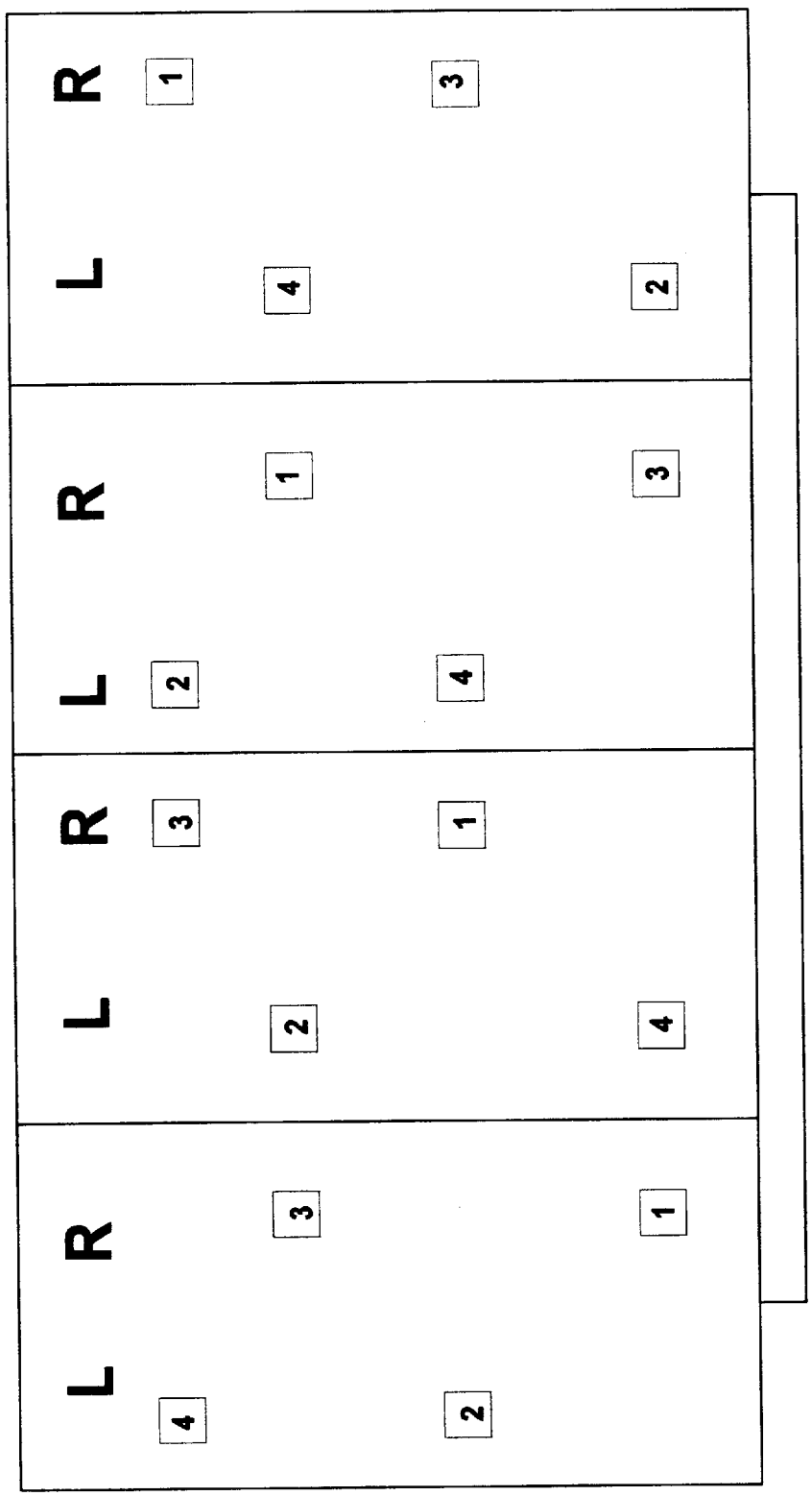
FIG. 11 is a set of four screen displays that cycle sequentially.

FIG. 11 shows four screen displays that cycle sequentially. The boxed numbers 1–4 are the moving feet target/actual positions. The bottom row shows the next target, which is arranged with respect to the previous actual position of row 2. The top row targets are discarded graphically. Data is retained as previously described for use in the appropriate calculations that measure performance characteristics. FIG. 12 is an exercise graphic report screen display which graphically shows average right and left leg steps and average step lengths.

The following table are examples of belt speed as a function (Step length, gait)

| STEP LENGTH [CM] | STEP LENGTH [FT] | GAIT CADENCE [CPS] | BELT SPEED FT/SEC | BELT SPEED [MPH] |
|---|---|---|---|---|
| 75.00 | 2.46 | .05 | 0.25 | 0.17 |
| 75.00 | 2.46 | .10 | 0.49 | 0.34 |
| 75.00 | 2.46 | .25 | 1.23 | 0.84 |
| 75.00 | 2.46 | .50 | 2.46 | 1.68 |
| 75.00 | 2.46 | .75 | 3.69 | 2.52 |
| 75.00 | 2.46 | 1.00 | 4.92 | 3.36 |
| 75.00 | 2.46 | 1.25 | 6.15 | 4.19 |
| 75.00 | 2.46 | 1.50 | 7.38 | 5.03 |
| 75.00 | 2.46 | 1.75 | 8.61 | 5.87 |
| 75.00 | 2.46 | 2.00 | 9.84 | 6.71 |
| 75.00 | 2.46 | 2.25 | 11.07 | 7.55 |
| 75.00 | 2.46 | 2.50 | 12.30 | 8.39 |

The instrumentation of the gait training treadmill bed is designed to determine when the left and when the right foot strike the surface of the belt. Knowing the belt speed time between foot falls and footfall position determines the step length.

Figure 13:
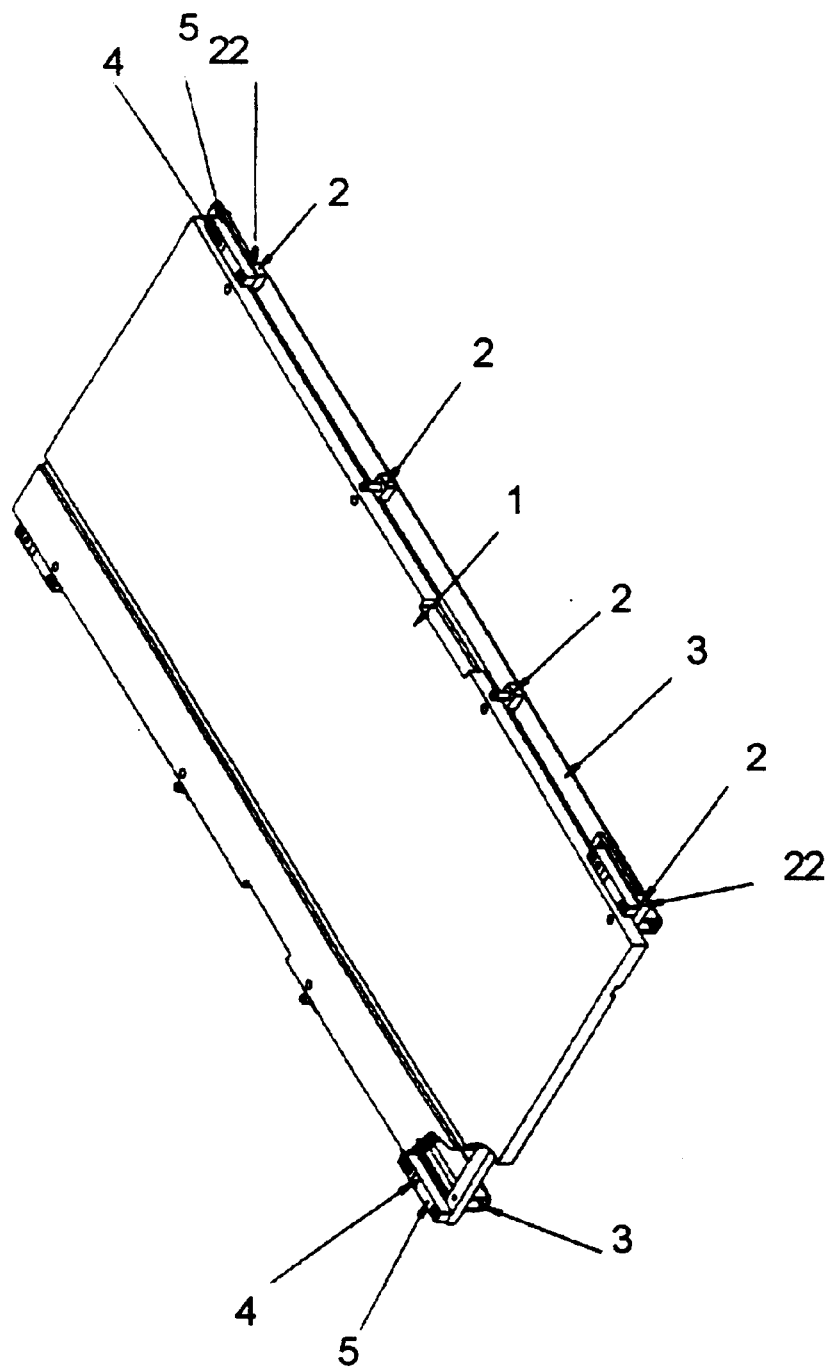
FIG. 13 is a schematic diagram of the treadmill bed.

The bed 1 (FIG. 13) of the treadmill may be comprised of composite material board that the tread belt slides over. It supports the belt and the user. The weight of the user is transferred to the bed 1 then from the bed 1 to the support frame then to the floor. The bed 1 is bolted to four cross braces 2. The cross braces 2 are joined by a support tube 3 on each side. In this way the cross braces 2 and support tubes 3 fully support the bed.

Figure 14:
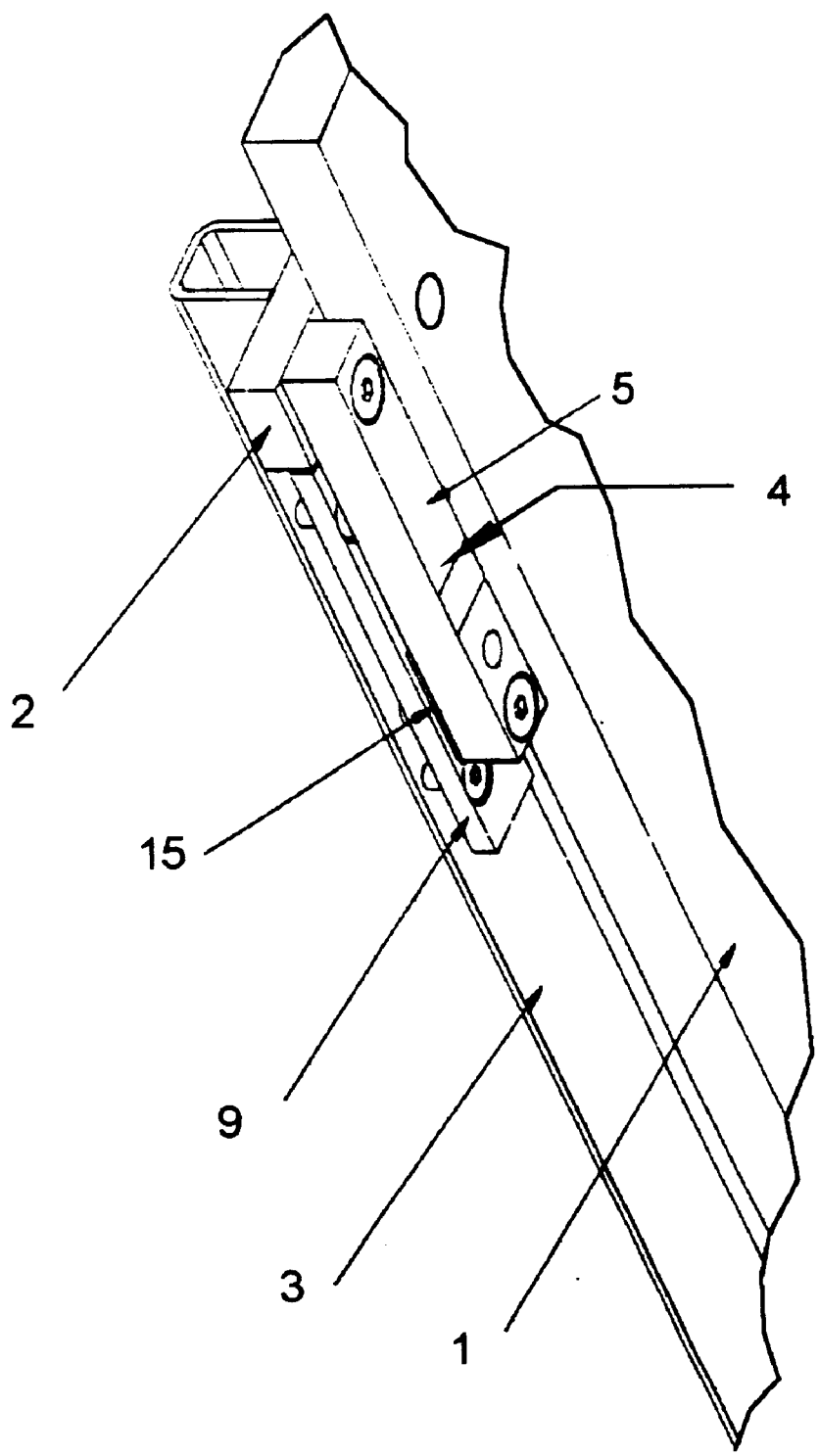
FIG. 14 is a schematic diagram of a support bar and base plate of the treadmill.
Figure 15:
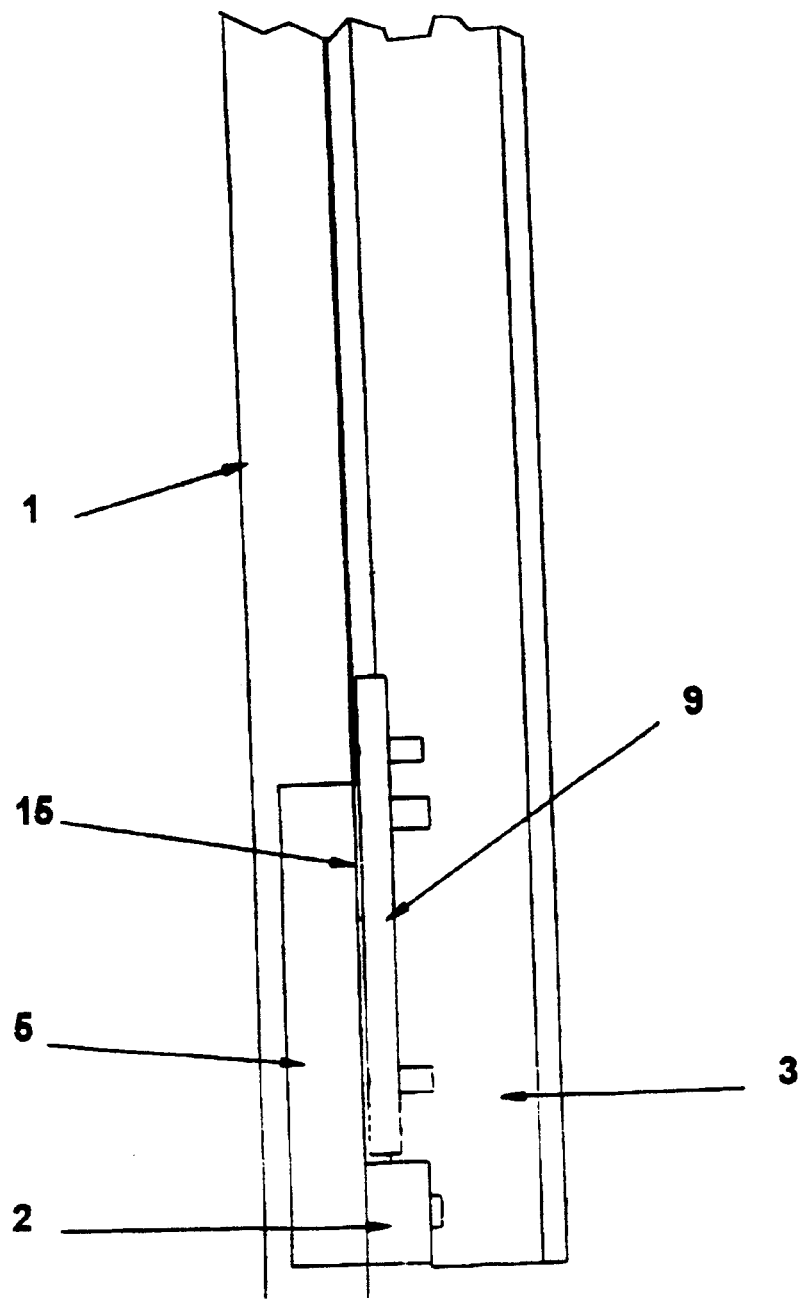
FIG. 15 is a schematic representation of a side view of the support bar and base plate of the treadmill.

The front and rear cross braces 22 are attached to four bars 5 which have strain gages 4 mounted to them. Each bar 5 is mounted to a base plate 9 (FIG. 14). In this fashion, the bars 5 carry the entire load of the bed 1 and any forces placed on the bed. The bars 5 are held slightly off the base plates 9 by spacers 15 (FIG. 15) so that the bars 5 have room to slightly defect to allow the strain gages 4 to measure the relative load carried by each of the bars 5.

It should be noted that at no time are the absolute forces applied by the users foot resolved and displayed. Force measurements are qualitative, not quantitative. The strain gages 4 are used only to determine the time and position of the foot fall and which foot has fallen. This is the only information used to determine cadence and step length. These parameters are used to control treadmill speed.

When a patient is walking, the right foot strikes the bed 1 farther to the right side than the left foot does. This holds true until a patient starts to run, when the footfalls can occur in line or even cross over. The signals from the four strain gages 4 are measured separately using standard electronic hardware, converted to separate digital signals and fed to a micro possessor. The signals of the right side gages and the left side gages are summed using a software algorithm. If the patients weight is placed on the left foot, the force is applied farther to the left on the bed. The bars 5 on the left side carry more load than they were because the left foot strikes further to the left. Thus, the total force carried by the right side bars 5 drops. The sum of the signals from the left strain gages goes up as the left foot just hit. The right foot hits and the sum of the right strain gages goes up. It can be seen that this holds true wherever the patient is walking on the bed- forward, back, left side and right side. As long as the feet are not crossing over, the system works.

To determine actual stride length however, more information is needed. Because the digital signals from the strain gages are kept separate, other information can be examined. Using standard force equations, the relative front to back position at which the force is being applied to the bed (foot position) can be determined. It must be noted that the true foot position can only be determined when only one foot is in contact with the bed. When walking, the front heel strike occurs when the rear foot is still in contact with the bed. The system described above can determine when the heel strike occurred but not where it occurred immediately. At some point after the back foot leaves the bed (when the determination of forces shows the front most position), the exact front to back position of the foot in contact is determined. The time of the heel strike is known as noted, the exact speed of the belt is known so the exact point of the foot when the heel strike occurred can be determined. The time of the heel strike is now known, as is the position. The time of the next heel strike is determined and likewise the position of the next heel strike. Knowing the time and position of the prior heel strike, the position of that foot is determined when the next heel strike occurs knowing that the foot was in contact with the belt the entire time and knowing the exact speed of the belt. The distance between the new heel strike and the foot position of the prior foot when the heel strike occurred is the step length.

Figure 16:
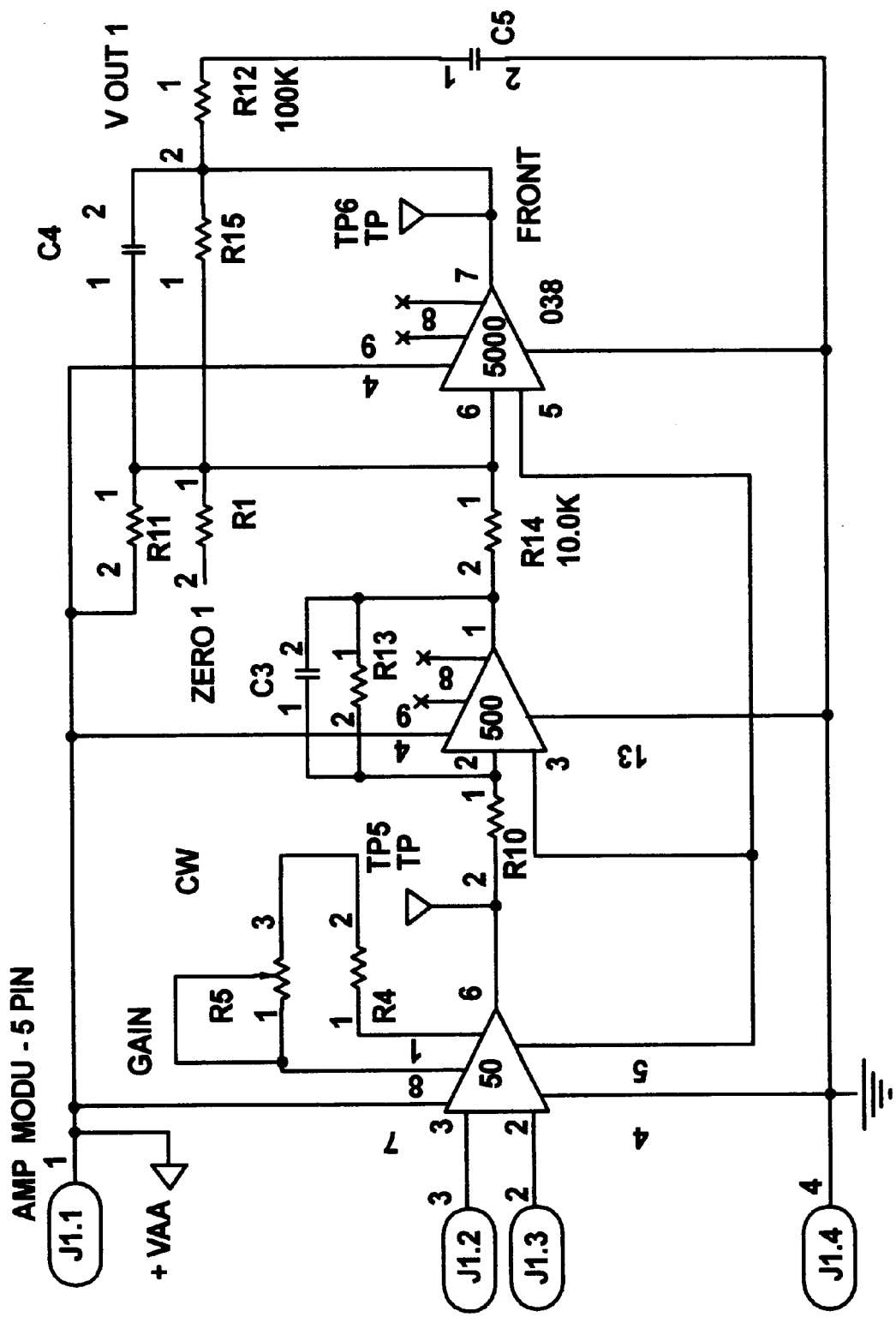
FIG. 16 is a schematic diagram of circuitry that electrically amplifies the strain gauge output of the treadmill.

FIG. 16 is a diagram of circuitry that electrically amplifies the strain gage output of the treadmill. Four circuits are used, one for each of the front, middle front, middle rear and rear of the treadmill.

Figure 17:
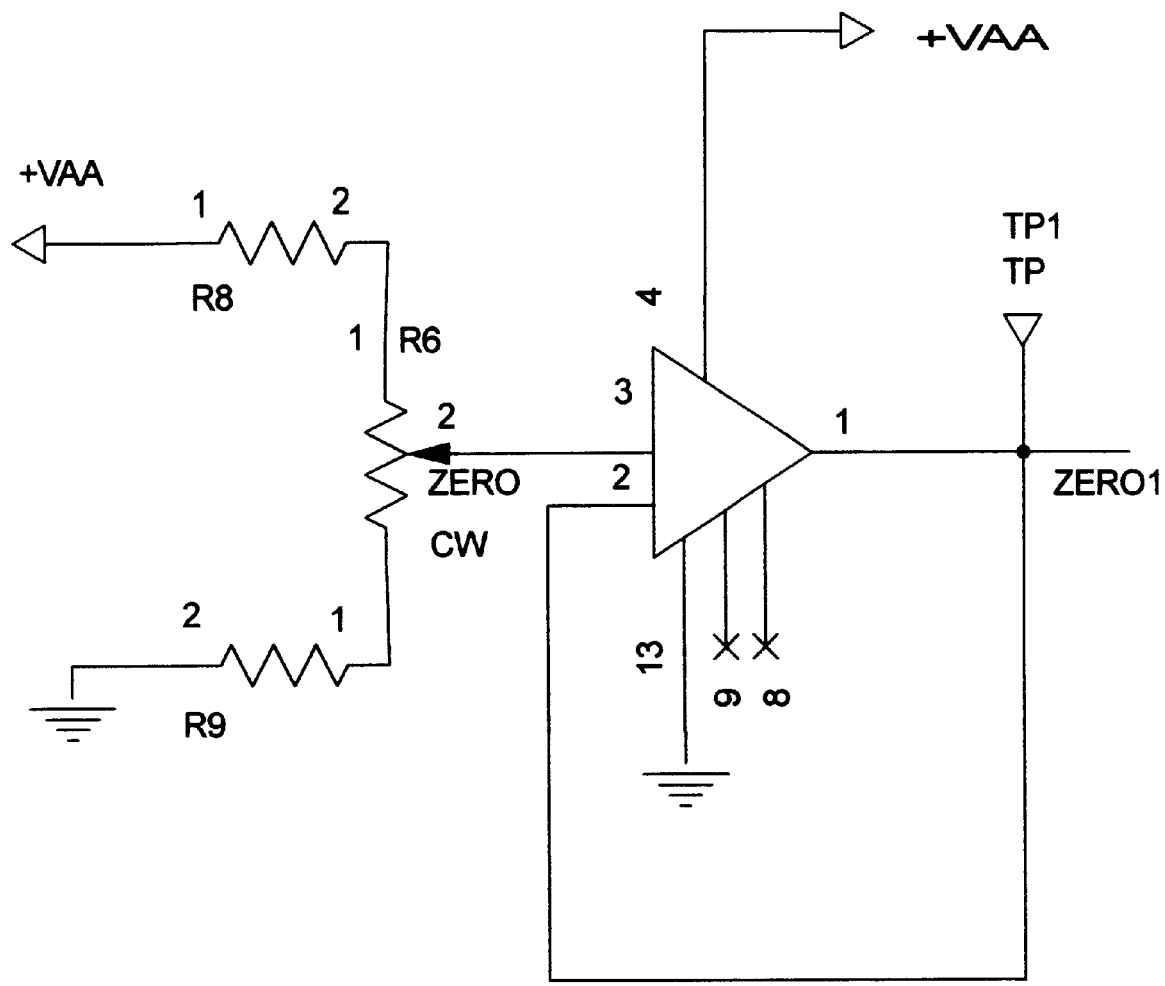
FIG. 17 is a schematic diagram of calibration adjusting circuitry for the treadmill.

FIG. 17 is a schematic diagram of strain gage nulling circuitry for the treadmill. Four circuits may be used, one for each of the front, middle front, middle rear and rear of the treadmill. Other circuit configurations that vary in scheme and number may be used in accordance with manufacturing and other preference.

While the foregoing description and drawings represent the preferred embodiments of the present invention, it will be understood that various changes and modifications may be made without departing from the spirit and scope of the present invention.

What is claimed is:

1. A gait rehabilitation aid, comprising:
   a treadmill belt having a belt speed;
   a user input device; and
   a controller responsive to entry into the user input device of information pertaining to any one of cadence and leg length to set the belt speed to match an appropriate step cycle that is based on the information.

2. An aid as in claim 1, wherein the controller includes a processor and a sensor, the sensor being configured and arranged to sense data related to gait parameters, the processor being responsive to the sensed data to provide an evaluation of the data with respect to stride length, cadence, gait velocity and gait pattern.

3. An aid as in claim 2, further comprising a printer in communication with the processor to print out the evaluation in response to appropriate signals generated from the user input device.

4. An aid as in claim 1, wherein the user input device includes a menu-driven screen display that displays the information.

5. An aid as in claim 4, further comprising a processor, the menu-driven screen display being responsive to the processor to scroll ideal foot prints in accordance with the appropriate step cycle.

6. An aid as in claim 4, further comprising a processor, the menu-driven screen display being responsive to the processor to show results of an evaluation by the processor with respect to gait parameters.

7. An aid as in claim 4, wherein the menu-driven screen display shows any of the entered leg length for both right and left legs, normal step length for both the right and left legs, coefficient of variance for both the right and left legs and a right/left time distribution percentage.

8. An aid as in claim 4, further comprising a processor, the menu-driven screen display being responsive to the processor to indicate an ambulation index value based on an evaluation by a processor of data pertaining to gait parameters.

9. An aid as in claim 5, further comprising a processor, the menu-driven screen display being responsive to the processor to sequentially cycle screen displays each showing representations of foot falls in accordance with the appropriate step cycle.

10. An aid as in claim 1, further comprising a display that shows representations of foot falls corresponding to actual foot falls on the treadmill belt together with ideal foot prints that scroll in accordance with the appropriate step cycle.

11. An aid as in claim 1, further comprising a processor, the menu-driven display being responsive to the processor to provide visual prompts to aid in improving gait characteristics said processor sending feedback to a menu drive display to provide a visual prompt in response to a sensor being configured and arranged to sense data with respect to gait parameters.

12. An aid as in claim 10, further comprising a printer in communication with the processor to print a summary of gait parameters corresponding to the actual foot falls and ideal foot prints.

13. An aid as in claim 2, wherein the controller includes a processor and a sensor, the sensor being configured and arranged to sense data related to the separate impacts of right and left foot strikes on the treadmill, the processor being responsive to the sensed data to provide an evaluation of the data with respect to the force of the impact by the foot strikes.

14. A method of aiding gait rehabilitation, comprising the steps of: setting treadmill belt speed to match an appropriate step cycle based on one of measured leg length and cadence;

running the treadmill belt to increase speed until reaching the set treadmill belt speed; and scrolling foot prints in a display in accordance with the appropriate step cycle.

15. A method as in claim 14, further comprising the step of monitoring gait parameters during the running of the treadmill belt and evaluating the gait parameters with respect to stride length, cadence, gait velocity and gait pattern.

16. A method as in claim 15, further comprising the step of printing the evaluated gait parameters.

17. A method as in claim 14, further comprising displaying foot falls corresponding to actual foot falls on the treadmill belt on a display screen together with the scrolling foot prints.

18. A method as in claim 14, further comprising measuring the leg length and entering values into a user input device of the measuring of the leg length, the setting of the treadmill belt speed being based on the entered values.

19. A method as in claim 14, further comprising measuring the force of right and left foot strikes on the treadmill and optionally the difference between the forces of the foot strikes.

20. The method of claim 19, further comprising evaluating the forces or differences between said forces.

21. A gait rehabilitation aid, comprising:

a treadmill having a belt speed;

a user input device;

a display screen;

a sensor arranged in the treadmill to sense a gait parameter; and a processor responsive to the sensor to direct the display screen to display a representation of a foot fall corresponding to the sensed gait parameter, the processor being responsive to the user input device to change the belt speed of the treadmill.

22. An aid as in claim 21, wherein the processor is responsive to the user input device to scroll a pattern of foot prints on the display screen based on entry of information into the user input device.

23. An aid as in claim 22, wherein the information is values corresponding to one of leg length and cadence.

24. A method of aiding gait rehabilitation, comprising the steps of:

entering information via a user input device that is one of leg length and cadence;

determining an appropriate step cycle based on the information;

running a treadmill belt at a speed that matches the appropriate step cycle;

sensing foot falls on a belt of the treadmill; and depicting representations of the foot falls on a display screen.

25. A method as in claim 21, further comprising:

scrolling ideal foot prints on the display in accordance with the appropriate step cycle; and varying step lengths to match the depicted representations of the sensed foot falls with the ideal foot prints scrolling on the screen.

* * * * *